(12) United States Patent
Haid, Jr. et al.

(10) Patent No.: US 7,799,053 B2
(45) Date of Patent: Sep. 21, 2010

(54) OCCIPITAL AND CERVICAL STABILIZATION SYSTEMS AND METHODS

(75) Inventors: Regis W. Haid, Jr., Atlanta, GA (US); Gregory C. Marik, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 440 days.

(21) Appl. No.: 10/795,880

(22) Filed: Mar. 8, 2004

(65) Prior Publication Data
US 2005/0197660 A1 Sep. 8, 2005

(51) Int. Cl.
*A61B 17/70* (2006.01)
(52) U.S. Cl. .................................................. 606/246
(58) Field of Classification Search ............. 606/60–63, 606/65–68, 246, 259, 300, 86 R, 86 A, 99; 403/204, 215; 411/44, 70, 57.1, 58, 60.1, 411/60.2
See application file for complete search history.

(56) References Cited

U.S. PATENT DOCUMENTS

| | | | | |
|---|---|---|---|---|
| 2,381,050 A | * | 8/1945 | Hardinge | 606/65 |
| 2,490,364 A | * | 12/1949 | Livingston | 606/68 |
| 2,699,774 A | * | 1/1955 | Livingston | 606/65 |
| 3,678,925 A | * | 7/1972 | Fischer et al. | 606/68 |
| 3,716,051 A | * | 2/1973 | Fischer | 606/68 |
| 3,760,802 A | * | 9/1973 | Fischer et al. | 606/63 |
| 3,805,775 A | | 4/1974 | Fischer et al. | |
| 4,541,423 A | | 9/1985 | Barber | |
| 4,790,303 A | | 12/1988 | Steffee et al. | |
| 4,854,312 A | * | 8/1989 | Raftopoulos et al. | 606/68 |
| 5,269,785 A | | 12/1993 | Bonutti | |
| 5,489,284 A | | 2/1996 | James et al. | |
| 5,545,164 A | | 8/1996 | Howland | |
| 5,591,235 A | | 1/1997 | Kuslich et al. | |
| 5,855,579 A | | 1/1999 | James et al. | |
| 5,908,423 A | | 6/1999 | Kashuba et al. | |
| 6,056,749 A | | 5/2000 | Kuslich | |
| 6,226,548 B1 | | 5/2001 | Foely et al. | |
| 6,287,313 B1 | | 9/2001 | Sasso | |
| 6,419,678 B1 | | 7/2002 | Asfora | |
| 6,436,119 B1 | | 8/2002 | Erb et al. | |
| 6,498,421 B1 | | 12/2002 | Oh et al. | |
| 6,530,929 B1 | | 3/2003 | Justis et al. | |
| 6,607,530 B1 | | 8/2003 | Carl et al. | |
| 2001/0027320 A1 | | 10/2001 | Sasso | |
| 2002/0120270 A1 | | 8/2002 | Trieu et al. | |
| 2002/0161368 A1 | * | 10/2002 | Foley et al. | 606/61 |
| 2002/0165544 A1 | | 11/2002 | Perren et al. | |
| 2003/0158557 A1 | | 8/2003 | Cragg | |
| 2003/0204189 A1 | | 10/2003 | Cragg | |
| 2006/0009767 A1 | | 1/2006 | Kiester | |
| 2006/0036259 A1 | | 2/2006 | Carl et al. | |
| 2007/0191846 A1 | | 8/2007 | Bruneau et al. | |

* cited by examiner

FOREIGN PATENT DOCUMENTS

WO    WO 00/67651    11/2000

*Primary Examiner*—Eduardo C Robert
*Assistant Examiner*—David Comstock

(57) ABSTRACT

A spinal stabilization system comprises an elongated stabilization device including a curved configuration along a longitudinal axis thereof. The elongated stabilization device includes a length and cross-section sized for positioning through a pathway formed from an opening in a lateral mass of a first vertebra and into the first vertebra, through the facet joint formed by adjacent articular surfaces of the first vertebra and an adjacent bony structure, and into the adjacent bony structure. Instruments can be provided to form the pathway and insert the stabilization device into the pathway.

30 Claims, 5 Drawing Sheets

OCCIPITAL AND CERVICAL STABILIZATION SYSTEMS AND METHODS

BACKGROUND

Various devices have been employed for fixation of the cervical vertebrae, and for fixation of the occiput with the cervical vertebrae. Posterior systems include a plate attached to the occiput with screw fixation, typically in the posterior-medial section of the occiput. A rod extends from the plate and along the C1, C2 and even C3 vertebrae for attachment thereto to provide a platform for fixation. Spanning of multiple levels of the cervical spine results in fixation of these levels. However, for certain procedures fixation at one or more of these spanned levels of the cervical spine may not be desired.

In the cervical region, anatomical considerations make it difficult to utilize a trans-articular screw. Furthermore, to achieve the desired alignment for a trans-articular screw, long incisions in the tissue along the cervical region of the spine are necessary. This provides the exposure required for a proper trajectory for the surgical approach to insert the screw through the articular joint.

Sub-occipital and sub-laminar wiring techniques have also been employed to stabilize the cervical region during fusion. Wiring techniques can result in complications with intradural penetration. Plating systems lie very close to the surface of the skin and can require bi-cortical placement of screws.

Systems for occipital and cervical stabilization are needed that provide adequate stabilization, can be targeted to the vertebral level or levels in which stabilization is desired, and reduce the invasiveness and complexity of the procedure.

SUMMARY

According to one aspect, a spinal stabilization system comprises an elongated stabilization device with a curved configuration along a longitudinal axis thereof. The stabilization device includes a length and cross-section sized for positioning through a pathway. The pathway is formed from an opening in a lateral mass of a first vertebra and into the first vertebra, through a facet joint formed by adjacent articular surfaces of the first vertebra and an adjacent bony structure, and into the adjacent bony structure.

According to another aspect, a spinal stabilization system comprises an elongated stabilization device with a curved configuration along a longitudinal axis thereof. The stabilization device includes a length and cross-section sized for positioning through a pathway formed through a joint between adjacent bony structures. The stabilization device includes an elongated outer member and an elongated inner member. The inner member is movable in the outer member between a first position wherein the stabilization device includes a reduced profile for insertion in the pathway and a second position wherein the inner member engages the outer member to provide at least a portion of the stabilization device with an enlarged profile to engage bony tissue along the pathway.

According to a further aspect, a method for stabilizing adjacent bony structures includes: forming an opening in a lateral mass of a cervical vertebra; forming a curved pathway from the opening and through a facet joint formed by adjacent articular surfaces of the cervical vertebra and an adjacent bony structure; and positioning an elongated stabilization device through the opening and along the curved pathway to link the cervical vertebra with the adjacent bony structure.

These and other aspects will also be apparent from the following description.

DESCRIPTION OF THE ILLUSTRATED EMBODIMENTS

For the purpose of promoting an understanding of the principles of the invention, reference will now be made to the illustrated embodiments thereof and specific language will be used to describe the same. It will nevertheless be understood that no limitation of the scope of the invention is thereby intended. Any such alterations and further modifications in the invention, and any such further applications of the principles of the invention as described herein are contemplated as would normally occur to one skilled in the art to which the invention relates.

Stabilization of adjacent vertebrae is provided with placement of a stabilization device through adjacent articular surfaces of bony structures, such as the cervical vertebrae and occiput, linking one or more of the vertebrae and/or occiput to one another. The stabilization device includes a curved profile along its longitudinal axis to facilitate its placement along a pathway that includes a joint formed by adjacent articular surfaces while minimizing the invasiveness of the procedure required to accommodate placement of the stabilization device. Furthermore, placement of the stabilization device through the joint reduces moment loads on the stabilization device since the stabilization device is located along or adjacent to an axis of movement of the adjacent bony structures. The systems and procedures contemplate application in the cervical region of the spine and the occiput, although application in other regions of the spine are also contemplated. Stabilization can be targeted to the vertebral level or levels desired while motion of the adjacent, non-instrumented vertebral level or levels can be preserved. Stabilization can be completed along one or more vertebral levels in the same surgical procedure with one stabilization device, or with multiple stabilization devices. It is further contemplated that multiple stabilization devices can be positioned to stabilize a particular vertebral level.

Figure 1:
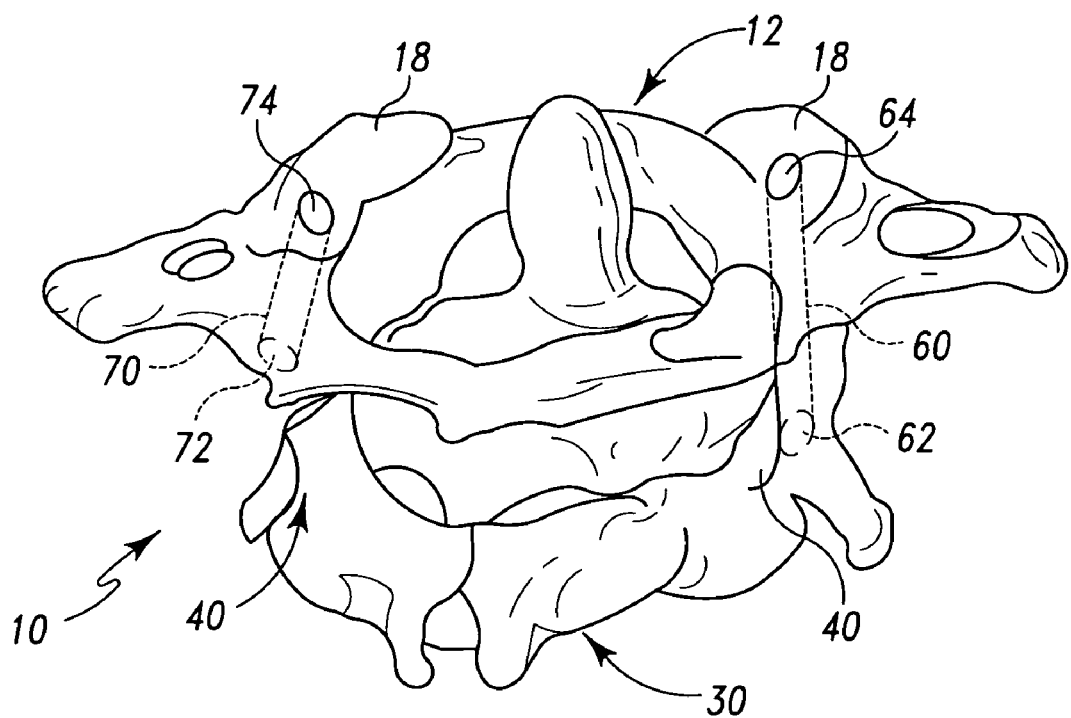
FIG. 1 shows an elevation view of a spinal column segment with pathways formed in the C1 and C2 vertebrae for insertion of stabilization devices.
Figure 2:
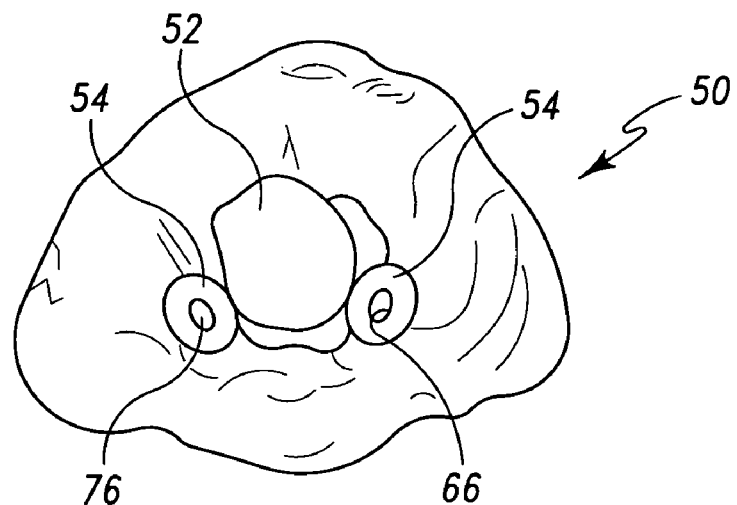
FIG. 2 shows a bottom view of an occiput with receptacles that comprise a portion of respective ones of the pathways of FIG. 1 formed for receipt of stabilization devices.

Referring to FIG. 1, there is shown a spinal column segment 10 including the upper cervical vertebra C1 designated at 12 and the next lower cervical vertebra C2 designated at 30. Occiput 50, shown in FIG. 2, resides at the superior end of C1 vertebra 12. Occiput 50 includes foramen magnum 52 and occipita condyles 54 on opposite sides of foramen magnum 52.

Figure 3:
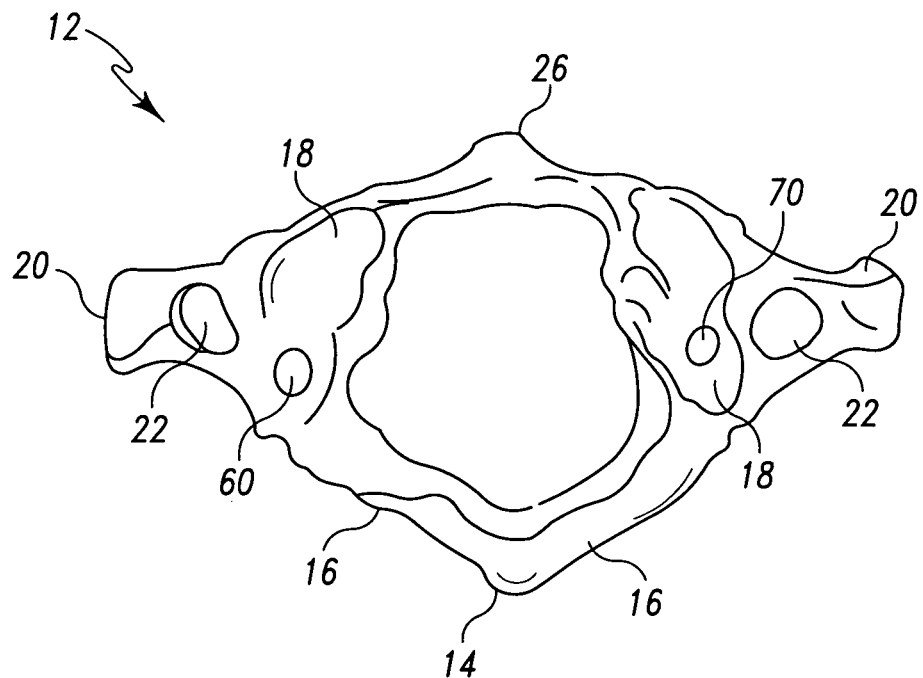
FIG. 3 is a superior plan view of the C1 vertebra showing the pathways of FIG. 1 opening at the superior articular facet.
Figure 4:
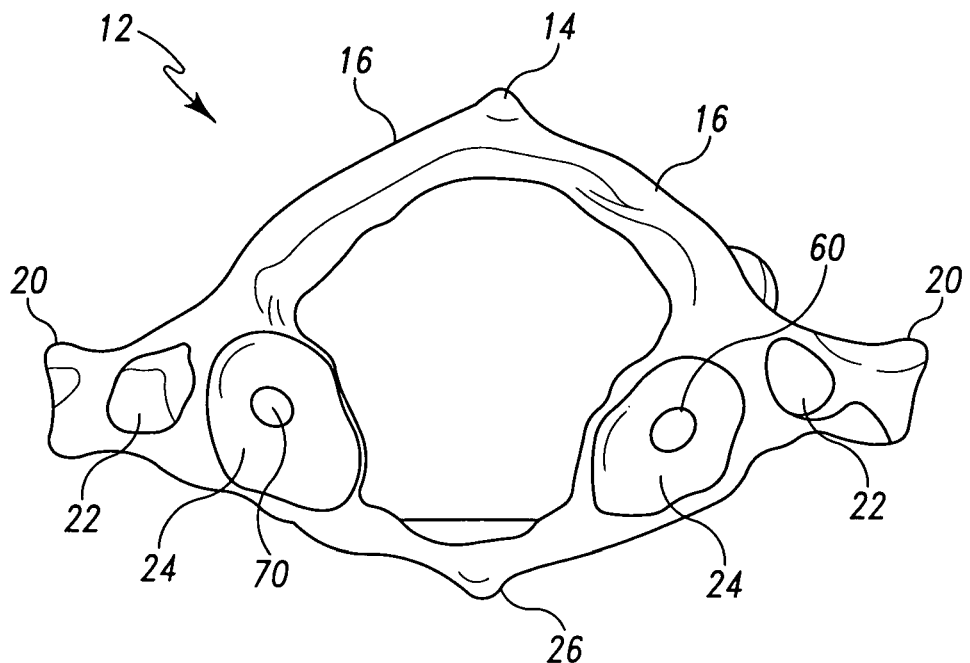
FIG. 4 is an inferior view of the C1 vertebra showing the pathways of FIG. 1 opening at the inferior articular facet.

Occipita condyles 54 are supported on and form a joint with respective ones of the superior articular facets 18 of C1 vertebra 12, shown in further detail in FIG. 3, a superior view, and in FIG. 4, an inferior view. The skull can articulate relative to C1 vertebra 12 about the joints formed between occipita condyles 54 and superior articular facets 18. C1 vertebra 12 includes posterior tubercle 14 and anterior tubercle 26. Laminae 16 extend from posterior tubercle 14 to respective lateral masses of the C1 vertebra 12. C1 vertebra 12 further includes transverse processes 20 and transverse foramen 22. Inferior articular facets 24 are supported on superior articular facets 44 of C2 vertebra 30.

Figure 5:
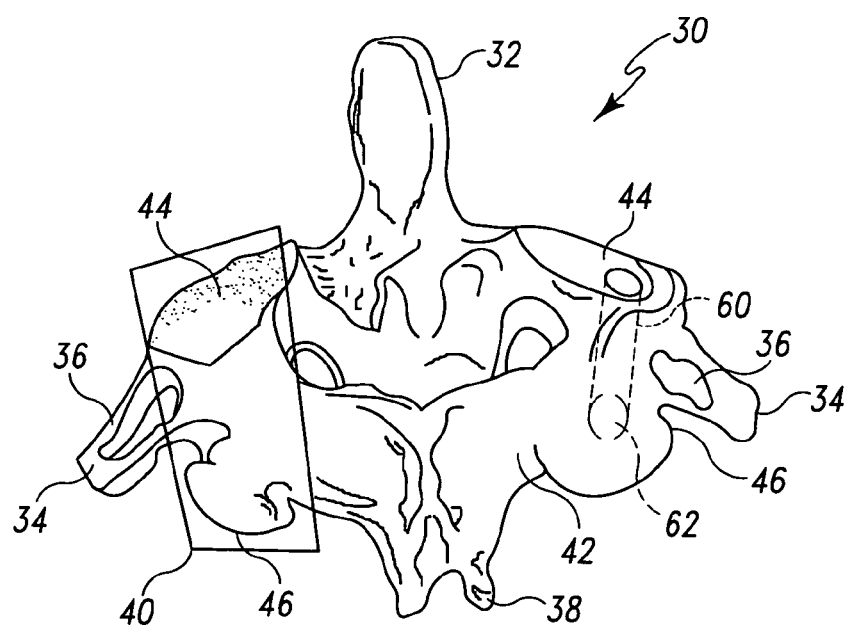
FIG. 5 is an elevation view of the C2 vertebra showing one pathway portion between the lamina and the superior articular facet.

C2 vertebra 30 is further shown in FIG. 5 in a posterior view, and includes odontoid process 32 along an anterior portion thereof. Spinous process 38 projects posteriorly from vertebra C2 and laminae 42 extend in opposite directions therefrom to lateral masses 40. Lateral masses 40 include a bony structure that forms superior articular facet 44 and inferior articular facet 46, which is oriented anteriorly for engagement with the superior articular facet of the C3 vertebra (not shown.)

A pair of insertion pathways for receiving stabilization devices is shown in FIGS. 1-5. A first insertion pathway 60 is provided from C2 vertebra 30, through C1 vertebra 12, and into occiput 50. A second insertion pathway 70 is shown from C1 vertebra 12 to occiput 50. It should be understood that surgical procedures are contemplated which employ identical insertion pathways 60 or 70 on each side of spinal column segment 10 and occiput 50; or a single insertion pathway 60 or 70 on one of the sides of spinal column segment 10 and occiput 50. It is further contemplated that insertion pathway 60 can terminate at a blind end in C1 vertebra 12 to provide stabilization only for the C1-C2 vertebral level. In any form, insertion pathways 60, 70 extend through the adjacent articulating surfaces of the facet joints to provide an avenue for insertion of a stabilization device. Insertion pathways 60, 70 are curved to accommodate the proper positioning of the stabilization devices relative to the anatomy of spinal column segment 10 and occiput 50, and to minimize the invasiveness of the procedure into the tissue in the approach to spinal column segment 10 for formation of pathways 60, 70.

In the illustrated embodiment, first insertion pathway 60 includes an inferior opening 62 in lateral mass 40 of C2 vertebra 30. Insertion pathway 60 extends from opening 62 through the bony structure of C2 vertebra 30, where it opens at the superior articular facet 44 of C2 vertebra 30. Insertion pathway 60 further extends through the facet joint into the inferior articular facet 24 of C1 vertebra 12. Insertion pathway 60 can terminate at a blind end in the lateral mass of C1 vertebra 12 for a single level stabilization of the C1 and C2 vertebrae 12, 30. In a further form, insertion pathway 60 can continue through the lateral mass of C1 vertebra 12 and through opening 64 at the superior articular facet 18 of C1 vertebra 12. Insertion pathway 60 extends through the joint between C1 vertebra 12 and occiput 50 into the aligned receptacle 66 formed in occiput condyle 54, where insertion pathway 60 terminates in a blind end.

In another embodiment, second insertion pathway 70 includes an inferior opening 72 in lamina 16 of C1 vertebra 12. Second insertion pathway 70 extends from opening 72 through the bony structure of C1 vertebra 12, where it opens at opening 74 in the superior articular facet 18 of C1 vertebra 12. Insertion pathway 70 extends through the joint between occiput 50 into the aligned receptacle 76 in occiput condyle 54, where insertion pathway 70 terminates in a blind end.

Figure 6:
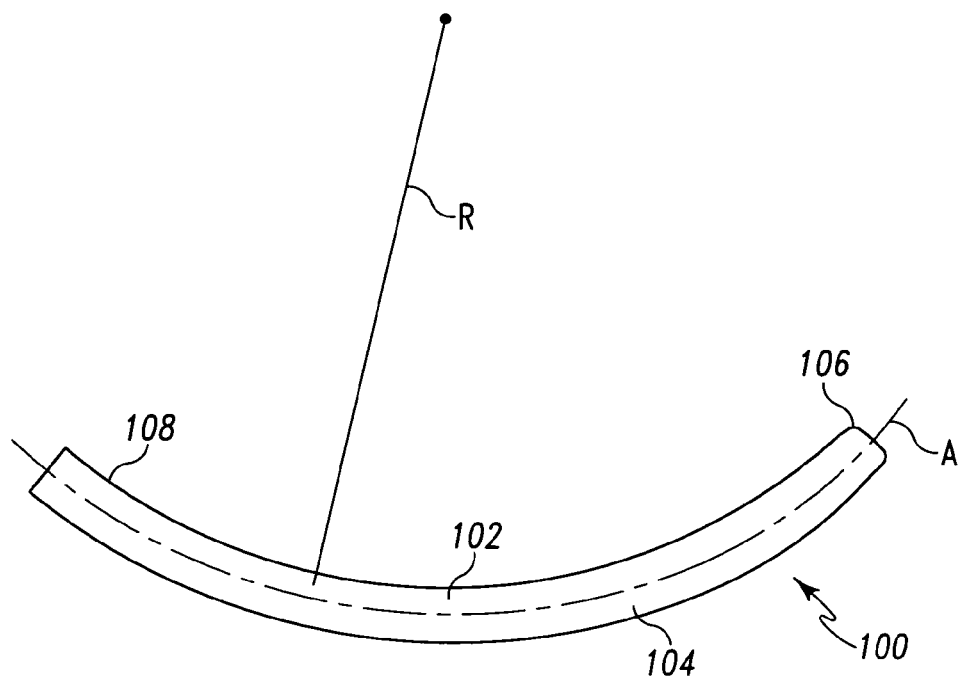
FIG. 6 is an elevation view of one embodiment stabilization device.

Referring now to FIG. 6, there is shown one embodiment of a stabilization device 100 for insertion in a pathway 60, 70. Stabilization device 100 includes a body 102 having a length extending along and curved along longitudinal axis 104. Body 102 extends between a leading end 106 and a trailing end 108. The curvature of body 102 between ends 106, 108 can be defined by a radius R to facilitate insertion along a pathway defined by an arc A formed about radius R. In the illustrated embodiment, stabilization device 100 is a rod or shaft curved at a single radius R along arc A, and longitudinal axis 104 is co-linear with arc A. However, it is contemplated that stabilization device 100 can have a curvature that differs from arc A, or can have a curvature that varies or is compounded along its length.

In the illustrated embodiment, body 102 can include a circular cross-sectional shape; however, other shapes are also contemplated, including oval, polygonal, square, rectangular, non-circular, and irregular cross-sections, for example. The cross-section can be of uniform dimension along the length of body 102, or can be tapered, stepped or otherwise varied to provide regions of greater and lesser dimension. Body 102 can be sized with a cross-section along at least a portion of the length thereof that is slightly greater than size of pathway 60, 70 to provide frictional engagement with the surrounding bony tissue. Body 102 can also be provided with a cross-sectional size that is about the same or less than the opening formed by pathway 60, 70. In still another form, body 102 can be provided with a cross-section, such as a non-circular cross-sectional shape, that differs from the shape of the opening formed by pathway 60, 70. Body 102 can include surface features extending along body 102 and/or transversely to longitudinal axis 104 that enhance engagement of body 102 with the adjacent bony tissue. Examples of surface features include knurlings, teeth, barbs, spikes, ridges, and/or grooves.

Stabilization device 100 can be rigid or semi-rigid, at least during placement, to facilitate placement through the pathways 60, 70 by pushing on the trailing end thereof to advance the leading end. In another form, body 102 is flexible and is mounted to a carrier for insertion through pathways 60, 70. Body 102 can be solid, or can include any one or combination of fenestrations, dimples, longitudinal passages, transverse passages, and through-holes. Body 102 can be comprised of a metal or metal alloy, such as stainless steel, titanium, or other suitable biocompatible metal material. In other forms, stabilization device can be an elastic or super-elastic member made from a super-elastic metal alloy, such as nitinol, or a polymer material.

Stabilization device 100 can be in the form of a cable, band or artificial ligament made from any suitable bio-compatible material, and employed to tether the bony structures to one another through pathways 60, 70. In still further forms, body 102 can be comprised entirely or partially of resorbable material, or of porous material, to facilitate integration with the bony tissue surrounding body 102. In still a further form, body 102 can be comprised of ceramic material, or bone material, for example. Body 102 can be coated, impregnated, or otherwise be a carrier for bone growth promoting material and/or therapeutic substances to promote or provide bone growth and healing. In another form, body 102 is formed by placing a material in a first form in the formed pathway 60, 70, and then allowing the material to cure in situ to form a stabilization device.

Figure 7:
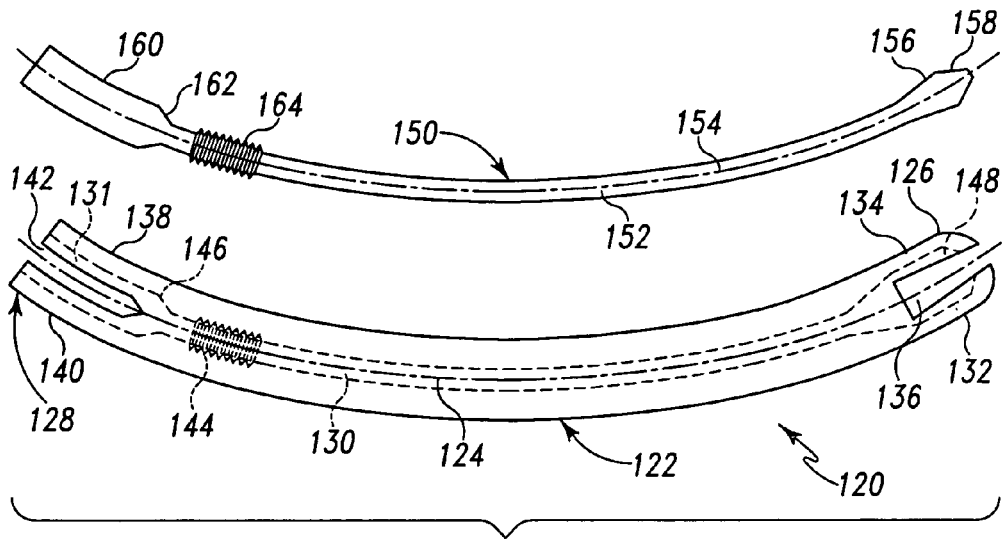
FIG. 7 is a disassembled view of another embodiment stabilization device.

In FIG. 7 there is shown another embodiment stabilization device 120, which can include any of the features and forms discussed above with respect to stabilization device 100. Stabilization device 120 includes an outer member 122 and an inner member 150. Outer member 122 includes a passage 130 extending along a longitudinal axis 124 thereof. Outer member 122 includes a leading insertion end 126 and an opposite trailing end 128. Passage 130 opens at trailing end 128, and at least extends adjacent to leading end 126. In the illustrated embodiment, passage 130 opens at leading end 126.

Inner member 150 includes an elongated body 152 extending between a leading end nose 156 and an intermediate nose 162 along longitudinal axis 154. An enlarged trailing end portion 160 extends from intermediate nose 162. Intermediate nose 162 includes a tapered surface profile that transitions between enlarged trailing end portion 160 and body 152. In the illustrated embodiment, a thread pattern 164 is formed along a portion of the length of body 152 adjacent intermediate nose 162. Leading end nose 156 includes an enlarged configuration relative to body 152, and includes tapered surfaces 158 extending therefrom toward the tip of inner member 150.

Figure 8:
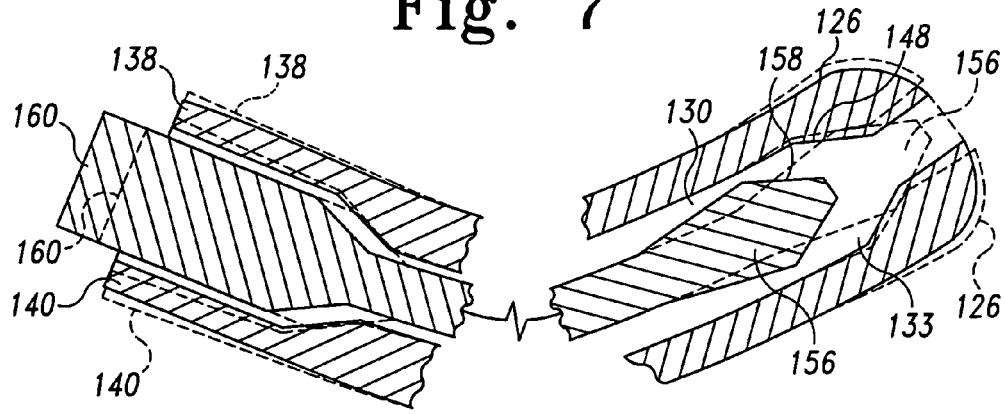
FIG. 8 is a detailed section view of a leading end and a trailing end of the stabilization device of FIG. 7 when assembled.

In use, inner member 150 is positioned in passage 130 of outer member 122. Outer member 122 can include thread pattern 144 along an inner wall surface thereof configured to threadingly engage thread pattern 164 of inner member 150, although non-threaded engagement between inner member 122 and outer member 150 is also contemplated. In the insertion configuration, as shown in FIG. 8, leading end nose 156 is positioned adjacent to leading end 126 of outer member 122 such that nose 156 is received in passage 130 adjacent a tapered leading end portion 133 thereof. Similarly, enlarged trailing end portion 160 is received in an enlarged trailing end portion 131 of passage 130. In this configuration, stabilization device 120 includes a reduced profile along the length thereof to facilitate insertion into pathways 60, 70.

When stabilization device 120 has been inserted in one of the pathways 60, 70, inner member 150 can be advanced in outer member 122 such that leading end nose 156 contacts tapered inner surface portion 148 of outer member 122 along leading end portion 133 of passage 130 as shown in dashed lines in FIG. 8. Leading end portion 126 includes a slot or relief 136 that provides at least two fingers 132, 134. Leading end nose 156 provides a wedge-effect and pushes on inner surface portion 148 to bias fingers 132, 134 away from one another and to deploy end nose 156 into firm engagement with the adjacent bony tissue of the pathway 60, 70 into which stabilization device 120 has been positioned.

Similarly, trailing end 128 of outer member 122 includes a slot or relief 142 that provides at least two fingers 138, 140 adjacent trailing end portion 128. The tapered surface of intermediate nose 162 contacts and pushes on intermediate tapered portion 146 of passage 130, providing a wedge effect that pushes fingers 138, 140 away from one another as shown in dashed lines in FIG. 8. Trailing end 128 is then deployed into engagement with the adjacent bony tissue of the pathways 60, 70 into which stabilization device 120 has been positioned.

In embodiments where inner member 150 is not threadingly engaged to outer member 122, inner member 150 can be configured to move longitudinally within outer member 122 to deploy one or more portions of it into engagement with the adjacent bony tissue. For example, inner member 150 can interface with outer member 150 via a snap fit, interference fit or other suitable coupling arrangement permitting longitudinal reciprocal movement of inner member 150 relative to outer member 122.

Figure 11:
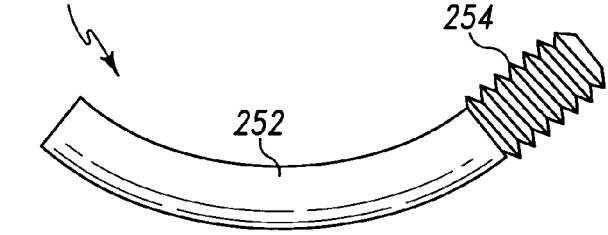
FIG. 11 is an elevational view of another embodiment stabilization device.

Still other stabilization device embodiments are contemplated. For example, in FIG. 11 there is shown stabilization device 250 including a curved body 252 and a leading end 254. Leading insertion end 254 includes a threaded nose configuration for engaging the adjacent bony tissue. Body 252 is sufficiently flexible and sized to permit rotation of body 252 to rotate leading insertion end 254. In another form, body 252 includes a central passage opening to leading insertion end 254. Leading insertion end 254 is rotatably coupled to body 252. A flexible driver can be positioned through the passage.

Figure 12:
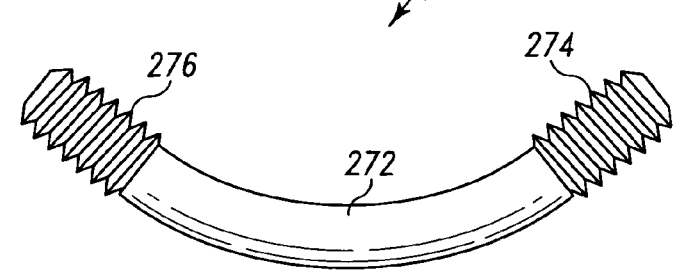
FIG. 12 is an elevational view of another embodiment stabilization device.

In another embodiment shown in FIG. 12, a stabilization device 270 is provided that includes a curved body 272 extending between a leading insertion end 274 and a trailing end 276. Each of the ends 274, 276 is provided with a threaded nose arrangement for engagement with the adjacent bony tissue. The pitch of the nose threads can be the same at each end, or can be different to provide either a distraction or compression effect as the threaded noses are engaged with the adjacent bony structure. A central lumen or passage can be provided through body 272 to leading insertion end 274 to receive a driver instrument. Body 272 can also be flexible between ends 274, 276 and sized to permit rotation of body 252 to rotate leading insertion end 254.

Figure 13:
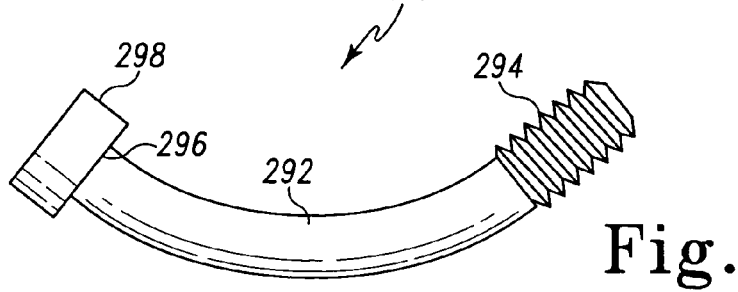
FIG. 13 is an elevational view of another embodiment stabilization device.

In FIG. 13 another embodiment stabilization device 290 is provided that includes a curved body 292 and a threaded leading insertion end 294. The trailing end 296 includes an enlarged contact member 298 projecting therefrom. Contact member 298 engages the bone about the entrance to the pathway formed therein when body 292 and insertion end 294 are positioned in the pathway. As insertion end 294 is threadingly engaged in the pathway, contact member 298 engages the bone to deliver a compression force between the adjacent bony structures along the pathway.

Figure 9:
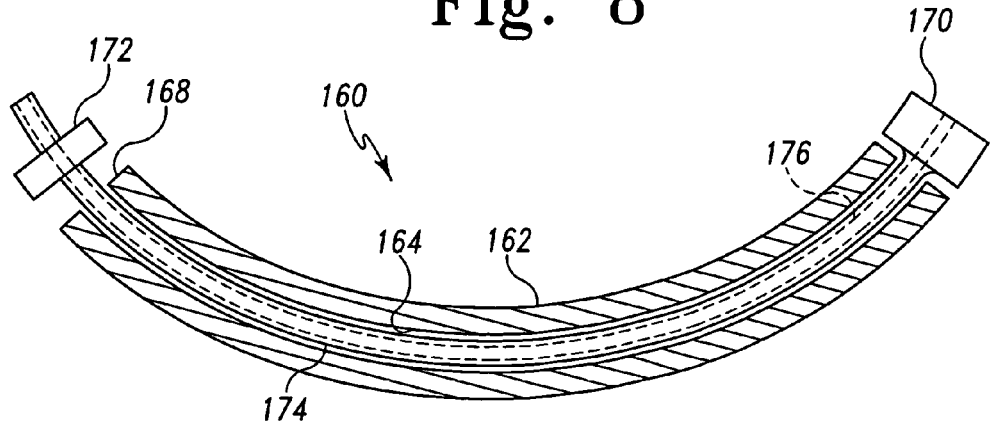
FIG. 9 is a sectional view of one embodiment of a drill instrument.

Various techniques and instruments for forming pathways 60, 70 are contemplated. For example, in FIG. 9 there is shown a cutting instrument 160 which includes an outer shaft 162 defining a passage 164 therethrough. A cutting head 170 is located adjacent a leading end 166 of outer shaft 162, and a coupler 172 is located adjacent to a trailing end 168 of outer shaft 162. A flexible drive member 174 extends between and interconnects coupler 172 with cutting head 170. A rotary power source (not shown) can be engaged to coupler 172, and operated to deliver a rotary force thereto. Rotation of coupler 172 is transmitted through drive member 174 to rotate cutting head 170. Cutting head 170 can be configured to drill or ream a pathway through bony material along the desired insertion path.

Outer shaft 162 is curved along its longitudinal axis to conform to the desired shape of the pathway 60, 70 to be formed therewith. Cutting head 170 removes bone material from the pathway 60, 70 which can deposited in passage 164 for evacuation. Drill instrument 160 can be guided through the bony structures to form pathway 60, 70 with image guidance technology employed during the surgical procedure. The pathway 60, 70 can further be defined through pre-operative X-rays or fluoroscopy to determine the appropriate location and trajectory for pathways 60, 70 prior to the surgical stabilization procedure. Outer shaft 162 can be bent, formed, controlled or manipulated so that the pathway of the desired shape, trajectory and length is formed.

In one embodiment, drive member 174 includes a central guide lumen 176 extending therethrough. Guide lumen 176 extends through cutting head 170 and also coupler 172. Guide lumen 176 can receive a guidewire or other device along which the cannulated drilling or reaming instrument 160 is to be moved to form the pathway along the desired trajectory.

Figure 10:
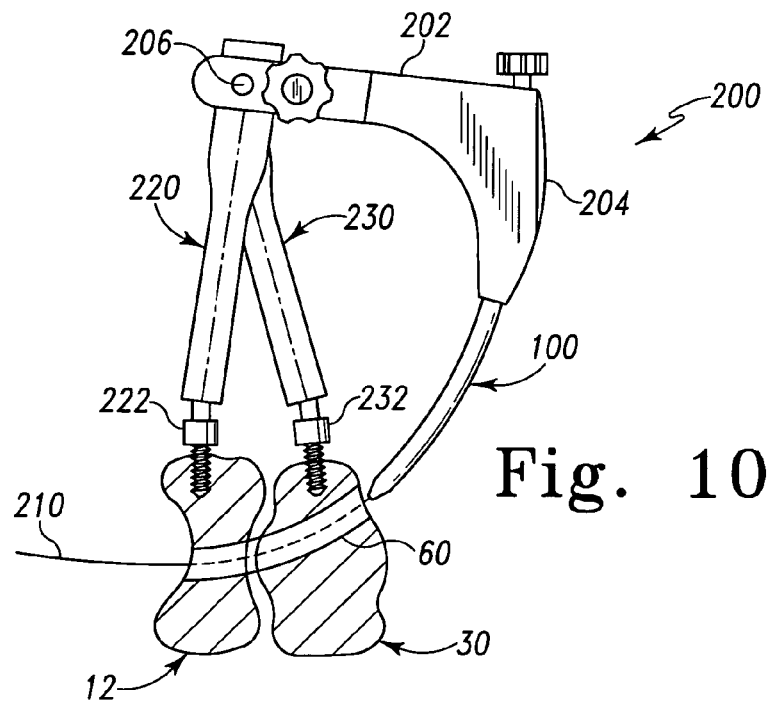
FIG. 10 is an elevational view of a spinal column segment with an insertion instrument mounted thereto to facilitate pathway formation and stabilization device placement.

After the pathway is formed, the stabilization device can be inserted into the pathway with freehand techniques or instruments, or with instruments that provide for controlled insertion. For example, FIG. 10 shows C1 vertebra 12 and C2 vertebra 30 in section along pathway 60. Although occiput 50 is not shown, it should be understood that, as discussed above, pathway 60 may extend into occiput 50. Furthermore, it should be understood that the discussion that follows also has application with pathway 70.

In the illustrated embodiment, C1 vertebra 12 and C2 vertebra 30 each include an anchor 222, 232, respectively, engaged thereto. A first anchor extension 220 extends from first anchor 222, and a second anchor extension 230 extends from second anchor 232. An insertion instrument 200 can be provided that is, in one embodiment, configured substantially as described in U.S. Pat. No. 6,530,929, which is hereby incorporated by reference in its entirety. Insertion instrument 200 includes a first portion 202 pivotally mounted to the anchor extensions 220, 230 about pivot axis 206. Insertion instrument 200 further includes a second portion 204 extending from and transversely oriented to first portion 202. First portion 202 is rotatable about the proximal ends of anchor extensions 220, 230 to swing second portion 204 along an arcuate axis 210.

First portion 202 includes a length extending from pivot axis 206 that corresponds to the radius or other shape required from pivot axis 206 to form pathways 60, 70 through the bony structures. Accordingly, the length of first portion 202 is sufficient to position second portion 204 and thus the stabilization device coupled thereto adjacent or below anchors 222, 232 and into the bony structure to which insertion instrument 200 is mounted.

A stabilization device, drill instrument, guidewire or other device can be delivered to the bony structure along the desired pathway. For example, stabilization device 100, as shown in FIG. 10, is releasably coupled to and extends from second portion 204. In this configuration, it is contemplated that longitudinal axis 104 of stabilization device 100 extends along arcuate axis 210. Accordingly, as first portion 202 is pivoted about pivot axis 206, second portion 204 and thus stabilization device 100 are moved along arcuate axis 210.

Other forms for insertion instrument 200 are contemplated. For example, insertion instrument 200 can be mounted to a single anchor engaged to the bony structure, or to more than two anchors. Suitable anchors include multi-axial screws, uni-axial screws, staples, tacks, stakes, pins, wires, posts or other device capable of suitably mounting the insertion instrument 200 to a bony structure.

In one technique, pathways 60, 70 are formed by positioning a guidewire through the bony structure along the desired pathway trajectory through the bony tissue. The guidewire insertion and positioning can be monitored via a surgical navigation system employing fluoroscopy or other suitable viewing instrumentation. Additionally, the guidewire can be coupled to an inserter, such as insertion instrument 200, to facilitate positioning along the pathway 60, 70. After insertion of the guidewire, a cutter or drill with a flexible shaft can be guided along the guidewire to form pathway 60, 70. In one form, drill instrument 160 can be provided with guide lumen 176 therealong to receive the guidewire as it is advanced along pathway 60, 70. Other embodiments contemplate a drill instrument with a central lumen for receiving the guidewire as the curved drill instrument is advanced therealong.

Various other instruments are also contemplated which can be coupled to drill instrument 160 to guide formation of pathway 60, 70. For example, U.S. Pat. No. 6,226,548 to Foley et al., which is hereby incorporated by reference, describes an optically tracked inserter device. Drill instrument 160 can be coupled to such an inserter device to provide image guided navigation of the drill instrument along the pathways 60, 70. The stabilization device can further be coupled to such an inserter device and inserted into the pathway 60, 70 to provided image-guided navigation and monitoring of the stabilization device insertion.

While the invention has been illustrated and described in detail in the drawings and foregoing description, the same is to be considered as illustrative and not restrictive in character. All changes and modifications that come within the spirit of the invention are desired to be protected.

What is claimed is:

1. A spinal stabilization system, comprising:
an elongated stabilization device including an elongated outer member and an elongated inner member movably received in said outer member, said inner and outer members each including a curved configuration along a longitudinal axis that extends along a length of said stabilization device between a leading end and an opposite trailing end of said stabilization device, said stabilization device further maintaining said curved configuration when in a collapsed insertion configuration and an expanded engagement configuration, wherein said curved configuration of each of said inner and outer members forms an arc along a length of said stabilization device and said arc and said longitudinal axis are co-linear along said length in each of said collapsed insertion configuration and said expanded engagement configuration, said stabilization device including a cross-section along said length with said length and cross-section sized for positioning through a pathway formable from an opening in a lateral mass of a first vertebra and into the first vertebra, through a facet joint formed by an articular surface of the first vertebra and an articular surface of an adjacent bony structure, and into the adjacent bony structure, wherein said inner member is movable in said outer member so that in said expanded engagement configuration a leading end and an opposite trailing end of said outer member are each expanded to engage bony tissue along the insertion pathway.

2. The system of claim 1, wherein said stabilization device is a rigid rod.

3. The system of claim 1, wherein said leading end of said elongated outer member is tapered for insertion into the pathway, and said elongated outer member includes a passage extending between said leading end and said trailing end thereof.

4. The system of claim 3, wherein said inner member is received in said passage, said inner member being movable between a first position wherein said leading end and said trailing end of said outer member are in said collapsed insertion configuration to a second position wherein each of said leading end and said trailing end of said outer member are in said expanded engagement configuration to engage bony tissue along the insertion pathway.

5. The system of claim 4, wherein said inner member includes a leading end nose with a tapered profile and said leading end nose is enlarged relative to a body portion of said inner member, said body portion extending from said leading end nose to an opposite trailing end portion of said inner member, and said outer member includes an inner surface along said passage with a tapered portion adjacent said leading end of said outer member, wherein in said second position said leading end nose engages said tapered portion of said passage to expand said leading end of said outer member.

6. The system of claim 5, wherein said trailing end portion of said inner member is enlarged relative to said body portion and includes an intermediate nose tapered between said enlarged trailing end portion and said body portion of said inner member, and said inner surface of said outer member includes an enlarged trailing end portion, wherein in said second position said intermediate nose of said inner member engages said inner surface of said passage at said enlarged trailing end portion of said outer member to radially expand said trailing end of said outer member.

7. The system of claim 6, wherein said inner member includes a threaded portion to threadingly engage a threaded portion of said inner surface along said passage.

8. The system of claim 6, wherein said intermediate nose and said leading end nose simultaneously engage respective portions of said inner surface of said passage to expand said leading end of said outer member and said trailing end of said outer member.

9. The system of claim 4, wherein said inner member includes an enlarged trailing end portion and an intermediate nose tapered between said enlarged trailing end portion and a portion of said inner member extending from said enlarged trailing end portion, wherein in said second position said intermediate nose of said inner member engages said outer member to expand said trailing end of said outer member into engagement with bony tissue along the pathway.

10. The system of claim 1, wherein said length and cross-section of said stabilization device are structured to extend through the pathway when the adjacent bony structure is a second vertebra.

11. The system of claim 1, wherein said length and cross-section of said stabilization device are structured to extend through the pathway when the adjacent bony structure is an occiput.

12. The system of claim 1, wherein said length and cross-section of said stabilization device are structured to extend through the pathway when the adjacent bony structure is a second vertebra, and the pathway is formed to extend through the second vertebra, through adjacent articular surfaces of the second vertebra and an occiput, and into the occiput.

13. The system of claim 1, further comprising:
a drill instrument including an outer shaft with a passage, a cutting device at a leading end of said outer shaft and a coupling member at a trailing end of said outer shaft for receiving a rotary force, further comprising a flexible inner member extending through said passage and coupling said cutting device to said coupling member, wherein said outer shaft includes a curved configuration corresponding to the curved configuration of said stabilization device and being operable to form the pathway for receiving the stabilization device.

14. The system of claim 1, further comprising:
an insertion instrument releasably engageable to said stabilization device; and
a pair of anchors engageable to respective ones of the first vertebra and the adjacent bony structure, said insertion instrument being pivotally mountable to said pair of anchors and movable relative thereto to guide said stabilization device along an arc co-linear with the pathway.

15. The system of claim 1, wherein said stabilization device includes:
a concave curvature along a side thereof with said concave curvature extending from said leading end to said trailing end; and
a convex curvature opposite said side with said convex curvature extending along said stabilization device from said leading end to said trailing end.

16. The system of claim 1, wherein said inner member includes a body portion extending between a leading end nose and an opposite trailing end portion, each of said leading end nose and said trailing end portion being enlarged relative to said body portion to engage said outer member in said expanded engagement configuration.

17. A spinal stabilization system, comprising:
an elongated stabilization device having a length extending along a longitudinal axis between a leading end and an opposite trailing end, said stabilization device including a cross-section sized for positioning through a pathway formed through a joint between adjacent bony structures, said stabilization device including an elongated outer member and an elongated inner member, said inner member being movable in said outer member between a first position wherein said stabilization device includes a reduced profile for insertion in the pathway and a second position wherein said inner member engages said outer member to provide at least a portion of said stabilization device with an enlarged profile for engagement to bony tissue along the pathway, wherein said inner member and said outer member each include a curved configuration along said longitudinal axis that extends along said length of said stabilization device between said leading end and said opposite trailing end of said stabilization device, and in said curved configuration each of said inner member and said outer member forms an arc that is co-linear with said longitudinal axis along said length of said stabilization device, wherein when said inner member is in said second position a leading end and an opposite trailing end of said outer member are each expanded to engage bony tissue along the insertion pathway.

18. The system of claim 17, wherein said length and cross-section are sized for positioning in the pathway when the pathway extends from an opening in a lateral mass of a first vertebra and into the first vertebra and through a facet joint formed by adjacent articular surfaces of the first vertebra and an adjacent bony structure and into the adjacent bony structure.

19. The system of claim 17, wherein said leading end of said outer member is tapered and said outer member includes a passage extending between said leading end and said trailing end for receiving said inner member.

20. The system of claim 19, wherein in said first position said leading insertion end and said trailing end of said outer member are in a collapsed insertion configuration, and in said second position each said leading insertion end and said trailing end are expanded to engage bony tissue along the pathway.

21. The system of claim 19, wherein said inner member includes a body portion extending from a leading end nose that is enlarged relative to said body portion and said leading end nose includes a tapered profile, and said outer member includes an inner surface along said passage with a tapered portion adjacent said leading insertion end, wherein in said second position said tapered leading end nose engages said tapered portion of said passage to expand said leading insertion end of said outer member.

22. The system of claim 21, wherein said inner member includes an enlarged trailing end portion opposite said leading end nose and an intermediate nose tapered between said enlarged trailing end portion and said body portion of said inner member, and said outer member includes an inner surface along said passage, wherein in said second position said intermediate nose of said inner member engages said inner surface of said passage to radially expand said trailing end of said outer member.

23. The system of claim 22, wherein said inner member includes a threaded portion to threadingly engage a threaded portion of said inner surface along said passage.

24. The system of claim 22, wherein said intermediate nose and said leading end nose engage respective portions of said inner surface of said passage to expand said leading insertion end of said outer member and said trailing end of said outer member.

25. The system of claim 19, wherein said elongated inner member includes an enlarged trailing end portion and an intermediate nose tapered between said trailing end portion and a portion of said elongated inner member extending from said enlarged trailing end portion, wherein in said second position said intermediate nose of said elongated inner member engages said elongated outer member to expand said trailing end of said elongated outer member and engage bony tissue along the pathway.

26. The system of claim 17, wherein said length and cross-section are sized for the adjacent bony structures to be first and second cervical vertebrae.

27. The system of claim 17, wherein said length and cross-section are sized for the adjacent bony structures to be a first cervical vertebra and an occiput.

28. The system of claim 17, wherein said length and cross-section are sized for the adjacent bony structures to be first and second cervical vertebrae and the occiput.

29. The system of claim 17, wherein said stabilization device includes:
   a concave curvature along a side thereof with said concave curvature extending from said leading end to said trailing end; and
   a convex curvature opposite said side with said convex curvature extending along said stabilization device from said leading end to said trailing end.

30. The system of claim 17, wherein said inner member includes a body portion extending between a leading end nose and an opposite trailing end portion, each of said leading end nose and said trailing end portion being enlarged relative to said body portion to engage said outer member in said enlarged profile.

* * * * *